United States Patent
Yang et al.

(10) Patent No.: US 11,258,102 B2
(45) Date of Patent: Feb. 22, 2022

(54) FLUORINATED IONIC LIQUIDS FOR MULTI-LAYER LI ION BATTERY APPLICATIONS

(71) Applicant: Robert Bosch GmbH, Stuttgart (DE)

(72) Inventors: Jin Yang, Pleasanton, CA (US); Hany Basam Eitouni, Oakland, CA (US); Tristan Palmer, San Francisco, CA (US)

(73) Assignee: Robert Bosch GmbH, Stuttgart (DE)

( * ) Notice: Subject to any disclaimer, the term of this patent is extended or adjusted under 35 U.S.C. 154(b) by 117 days.

(21) Appl. No.: 16/416,114

(22) Filed: May 17, 2019

(65) Prior Publication Data

US 2020/0365944 A1 Nov. 19, 2020

(51) Int. Cl.
| | |
|---|---|
| *H01M 10/0569* | (2010.01) |
| *C07D 213/18* | (2006.01) |
| *C07D 221/00* | (2006.01) |
| *H01M 4/62* | (2006.01) |
| *H01M 10/052* | (2010.01) |
| *H01M 10/0568* | (2010.01) |
| *H01M 10/0565* | (2010.01) |
| *H01M 4/02* | (2006.01) |

(52) U.S. Cl.
CPC ...... *H01M 10/0569* (2013.01); *C07D 213/18* (2013.01); *C07D 221/00* (2013.01); *H01M 4/625* (2013.01); *H01M 10/052* (2013.01); *H01M 10/0565* (2013.01); *H01M 10/0568* (2013.01); *H01M 2004/028* (2013.01); *H01M 2300/0025* (2013.01); *H01M 2300/0082* (2013.01)

(58) Field of Classification Search
CPC ............. H01M 4/625; H01M 10/0569; H01M 10/052; H01M 10/0565; H01M 10/0568; H01M 2300/0082; H01M 2300/0025; H01M 2004/028; C07D 213/18; C07D 221/00
See application file for complete search history.

(56) References Cited

U.S. PATENT DOCUMENTS

| | | | |
|---|---|---|---|
| 8,268,197 B2 | 9/2012 | Singh et al. | |
| 8,563,168 B2 | 10/2013 | Balsara et al. | |
| 8,889,301 B2 | 11/2014 | Balsara et al. | |
| 9,054,372 B2 | 6/2015 | Singh et al. | |
| 9,136,562 B2 | 9/2015 | Singh et al. | |
| 9,893,337 B2 | 2/2018 | Pratt et al. | |
| 2012/0321966 A1 | 12/2012 | Wallin et al. | |
| 2014/0113202 A1* | 4/2014 | Sun | H01M 10/0567 429/328 |
| 2019/0326579 A1* | 10/2019 | Ryu | H01M 10/052 |

FOREIGN PATENT DOCUMENTS

KR  10-2019-0122469  *  4/2018 ............. H01M 2/16

OTHER PUBLICATIONS

Singh et al. Inorganic Chemistry 2003 vol. 42 pp. 6142-6146), 2003. Online Aug. 23, 2003.*
Bonhote, "Hydrophobic, Highly Conductive Ambient-Temperature Molten Salts," Inorganic Chemistry, V35, p. 1168 (1996).
DelSesto, "Tetraalkylphosphonium-based ionic liquids," Journal of Organometallic Chemistry 690 (2005) 2536-2542.
Madria, "Ionic liquid electrolytes for lithium batteries: Synthesis, electrochemical, and cytotoxicity studies," J. of Power Sources, V234, p. 277(2013).
Singh, Bridged Tetraquaternary Salts from N,N'-Polyfluoroalkyl-4,4'-bipyridine, Inorganic Chemistry, V42, p. 7416 (2003).
Singh, "New dense fluoroalkyl-substituted imidazolium ionic liquids," Tetrahedron Letters, V43, p. 9497 (2002).
Singh, "Syntheses of the first N-mono- and N,NA-dipolyfluoroalkyl-4,4Abipyridinium compounds," Chem. Comm. p. 1366 (2003).
Xue, "Ionic Liquids with Fluorine-Containing Cations," Eur. J. Inorg. Chem. p. 2573 (2005).
Zhang, "Direct methylation and trifluoroethylation of imidazole and pyridine derivatives," Chem. Comm. p. 2334 (2003).

* cited by examiner

*Primary Examiner* — Anca Eoff
*Assistant Examiner* — Aaron J Greso
(74) *Attorney, Agent, or Firm* — Brooks Kushman P.C.

(57) ABSTRACT

Fluorinated ionic liquids have been prepared to be used as catholytes in lithium battery cells. Such ionic liquids are immiscible with polyethylene-oxide-based solid polymer electrolytes, which may be used as separators in such cells. Such catholytes can increase the lifetime and boost the performance of lithium battery cells.

6 Claims, 7 Drawing Sheets

FLUORINATED IONIC LIQUIDS FOR MULTI-LAYER LI ION BATTERY APPLICATIONS

BACKGROUND OF THE INVENTION

Field of the Invention

This invention relates generally to lithium batteries, and, more specifically, to the use of a variety of electrolytes in the same lithium battery to optimize its performance.

In order to be useful in a cell, an electrolyte is chemically compatible/stable with both the anode material and the cathode material. In addition, the electrolyte is electrochemically stable, that is, stable against reduction at the anode and oxidation at the cathode when the cell is at potential. These requirements are especially difficult to meet in lithium batteries because of the extreme reactivity of the lithium itself. When a liquid electrolyte is used, it permeates both the anode and the cathode, as well as the separator, so the one electrolyte must meet all criteria. Thus, some compromises must be made in choice of electrolyte, as the electrolyte that is best for the anode and the electrolyte that is best for the cathode may not be the same.

Thus, there is a clear need for a battery cell design in which different portions of the cell can contain different electrolytes, each optimized for its particular function, but all functioning together without compromising the overall operation of the cell.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1(a)-(f) is a schematic illustration of various negative electrode assemblies, according to embodiments of the invention.

FIG. 2(a)-(f) is a schematic illustration of various positive electrode assemblies, according to embodiments of the invention.

SUMMARY

An electrochemical cell is provided. In one embodiment of the invention, the cell has a negative electrode configured to absorb and release alkali metal ions, a positive electrode that has positive electrode active material, binder, a fluorinated ionic liquid catholyte, a first salt that contains the alkali metal, and, optionally, electronically conducting carbon, a separator layer that has a block copolymer electrolyte and a second salt that contains the alkali metal. The separator layer is disposed between the negative electrode and the positive electrode and facilitates ionic communication therebetween. The fluorinated ionic liquid catholyte is immiscible with the block copolymer electrolyte. The first salt and the second may or may not be the same. The fluorinated ionic liquid may be any of wherein X is selected from the group consisting of $CF_3SO_3$, $PF_6$, $BF_4$, FSI, FAP, BOB, DFOB, and TFSI; R is selected from the group consisting of hydrogen, alkyls, and branched alkyls; Rf is selected from the group consisting of perfluoropolyethers and $(CF_2)_a CF_3$, in which a is an integer greater than or equal to 2; and n is an integer greater than or equal to 1.

The block copolymer separator electrolyte has a first block that may be ionically conductive and that may include any of polyethers, polyamines, polyimides, polyamides, alkyl carbonates, polynitriles, polysiloxanes, polyphosphazines, polyolefins, polydienes, polyesters, and combinations thereof. The first block of the block copolymer electrolyte may include an ionically-conductive comb polymer, which comb polymer comprises a backbone and pendant groups. The backbone may include one or more of polysiloxanes, polyphosphazines, polyethers, polydienes, polyolefins, polyacrylates, polymethacrylates, and combinations thereof. The pendants may include any of oligoethers, substituted oligoethers, nitrile groups, sulfones, thiols, polyethers, polyamines, polyimides, polyamides, alkyl carbonates, polynitriles, polyesters, other polar groups, and/or combinations thereof.

The block copolymer separator electrolyte has a second block that may include any of polystyrene, hydrogenated polystyrene, polymethacrylate, poly(methyl methacrylate), polyvinylpyridine, polyvinylcyclohexane, polyimide, polyamide, polypropylene, polyolefins, poly(t-butyl vinyl ether), poly(cyclohexyl methacrylate), poly(cyclohexyl vinyl ether), poly(t-butyl vinyl ether), polyethylene, poly(phenylene oxide), poly(2,6-dimethyl-1,4-phenylene oxide) (PXE), poly(phenylene sulfide), poly(phenylene sulfide sulfone), poly(phenylene sulfide ketone), poly(phenylene sulfide amide), polysulfone, fluorocarbons, polyvinylidene fluoride, and copolymers that contain styrene, methacrylate, and/or vinylpyridine.

The alkali metal may be any of lithium, sodium, or magnesium. In one arrangement, the alkali metal includes lithium. The first salt and the second salt may each be selected independently from the group consisting of LiTFSI, LiFSI, LiPF$_6$, LiFAP, LiBF$_4$, LiClO$_4$, LiOTf, LiC(Tf)$_3$, LiBOB, and LiDFOB. The first salt and the second salt may or may not be the same. The negative electrode may include a lithium-containing metal or alloy such as Li, Li—Al, Li—Si, Li—Sn, and/or Li—Mg. In one arrangement, the negative electrode includes negative electrode active material particles, an anolyte, optional electronically conducting particles, and optional binder. The negative electrode active material may be a material such as silicon, silicon alloys of tin (Sn), nickel (Ni), copper (Cu), iron (Fe), cobalt (Co), manganese (Mn), zinc (Zn), indium (In), silver (Ag), titanium (Ti), germanium (Ge), bismuth (Bi), antimony (Sb), and chromium (Cr), silicon oxides, silicon carbides, graphite, and mixtures thereof. The anolyte may include a liquid electrolyte that is immiscible with the separator electrolyte. The anolyte may be a block copolymer electrolyte that is immiscible with the separator electrolyte.

The positive electrode may include electronically conducting carbon. The positive electrode active material may include lithium metal oxides or lithium metal phosphates. The positive electrode active material may include elemental sulfur or sulfur composites with carbon or electronically-conductive polymer. The positive electrode active material may be any of FeS$_2$, FeOF, FeF$_3$, FeF$_2$ and MoO$_3$, sulfur, lithium polysulfides, CuO, Cu$_2$O, FeO, Fe$_2$O$_3$, V$_6$O$_{13}$, VO$_2$, Li$_{1+x}$V$_3$O$_8$ (0≤x≤3), Ag$_x$V$_2$O$_5$ (0≤x≤2), Cu$_x$V$_4$O$_{11}$ (0≤x≤3), and VOPO$_4$, LiCoO$_2$, LFP, NCM, NCA, or mixtures thereof.

In another embodiment of the invention, an electrochemical cell is provided. The cell has a lithium-containing metal negative electrode foil, a separator layer that includes a block copolymer electrolyte as described above, and a first lithium salt, and a positive electrode that includes positive electrode active material, binder, optional electronically conducting particles, a fluorinated ionic liquid catholyte as described herein, and a second lithium salt. The fluorinated ionic liquid catholyte is immiscible with the block copolymer electrolyte. The separator layer is disposed between the negative electrode and the positive electrode and facilitates ionic communication therebetween.

DETAILED DESCRIPTION

The preferred embodiments are illustrated in the context of electrolytes in an electrochemical cell. The skilled artisan will readily appreciate, however, that the materials and methods disclosed herein will have application in a number of other contexts where optimizing electrochemical interactions between electrolytes and electrochemically active materials are important. These electrolytes can be useful in electrochemical devices such as capacitors, electrochemical/capacitive memory, electrochemical (e.g., dye sensitized) solar cells, and electrochromic devices.

These and other objects and advantages of the present invention will become more fully apparent from the following description taken in conjunction with the accompanying drawings.

In this disclosure, the terms "negative electrode," "NE," and "anode" are both used to describe "negative electrode." Likewise, the terms "positive electrode," "PE," and "cathode" are both used to describe "positive electrode." The term "anolyte" is used to describe the electrolyte in the anode. The term "catholyte" is used to describe the electrolyte in the cathode.

In this disclosure, the term "dry polymer" is used to describe a polymer with long chains that has not been plasticized by small molecules. Organic solvents or plasticizers are not added to such dry polymers.

Although not always mentioned explicitly, it should be understood that electrolytes, as described herein, include metal salt(s), such as lithium salt(s), to ensure that they are ionically conductive. Non-lithium salts such as other alkali metal salts or salts of aluminum, sodium, or magnesium can also be used. In general, salts that contain the metal ion that shuttles back and forth during electrochemical cell cycling are the ones that are used.

Molecular weights in this disclosure have been determined by the weight-averaged method.

An electrochemical cell has a negative electrode assembly and a positive electrode assembly with an ionically conductive separator in between. In one embodiment of the invention, the negative electrode assembly contains at least negative electrode active material and an electrolyte that has been chosen specifically for use with the negative electrode active material, referred to herein as the NE (negative electrode) electrolyte.

Figure 1:
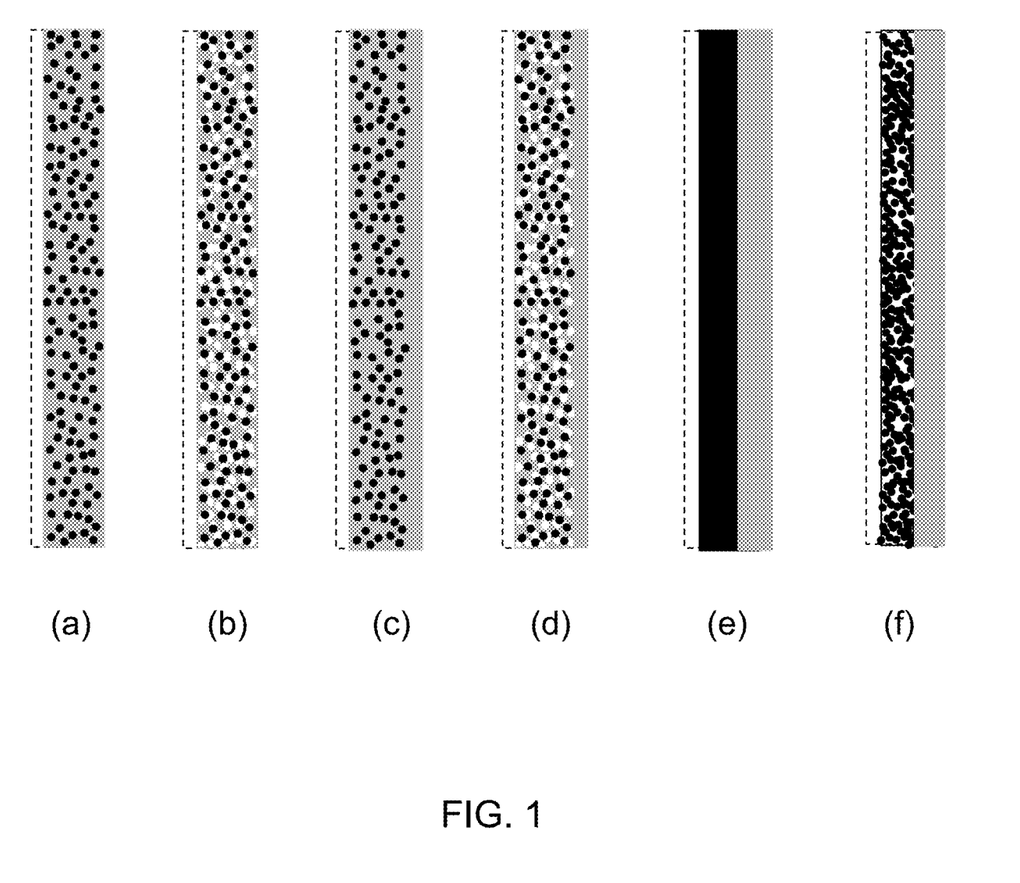

FIG. 1 illustrates various exemplary arrangements for negative electrode active material (black regions) and anolyte (grey regions). The negative electrode active material can be arranged as particles (FIGS. 1a-1d, 1f) or as a thin film or foil (FIG. 1e). The negative electrode assembly can be formed by combining the negative electrode material particles with the anolyte to form a composite layer (FIGS. 1a-1d). In some arrangements, other materials (not shown) can be added to the composite layer to enhance, for example, electronic or ionic conduction. In some arrangements, the composite is porous, i.e., contains voids which are shown as white spaces in FIGS. 1b, 1d; in other arrangements, the composite is pore-free (FIGS. 1a, 1c). In yet other arrangements, the dry polymer anolyte of FIGS. 1e and 1f may also contain pores (not shown). In a negative electrode assembly that has a composite layer, the dry polymer anolyte may be contained entirely within the composite layer (FIGS. 1a, 1b). In another arrangement, there can be a thin layer of additional NE dry polymer electrolyte adjacent the composite layer (FIGS. 1c, 1d). In some arrangements, a current collector (shown as a white layer defined by dashed lines) is also part of the negative electrode assembly.

In arrangements where the negative electrode active material is a thin film or foil, the negative electrode assembly contains at least the thin film or foil and a layer of the anolyte adjacent and in ionic contact with the thin film or foil, as shown in FIG. 1e. In some arrangements, the negative electrode material is not a solid thin film, but instead is arranged as an aggregation of negative electrode active material particles in close contact with one another to ensure ionic and electronic communication among the particles (FIG. 1f). Such a structure can be made, for example, by pressing and/or by sintering the negative electrode active material particles. In some arrangements, other materials can be added to the layer of negative electrode material particles, for example, to enhance electronic or ionic conductivity. In one arrangement carbon particles added to enhance electronic conductivity. The negative electrode assembly contains at least the anolyte layer in ionic communication with the layer of negative electrode active material particles. In some arrangements there is also a current collector (shown as a white layer defined by dashed lines) in electronic contact with the negative electrode assembly.

The anolyte is chosen specifically for use with the negative electrode active material. In one embodiment of the invention, the anolyte is a dry polymer (a polymer with long chains that has not been plasticized by any small molecules) electrolyte. The anolyte is electrochemically stable against the negative electrode active material. That is to say that the anolyte is reductively stable and resistant to continuous chemical and electrochemical reactions which would cause the anolyte to be reduced at its interface with the negative electrode material. The anolyte is resistant to reduction reactions over the range of potentials that the electrochemical cell experiences under conditions of storage and cycling. Such reduction reactions at the negative electrode would increase cell impedance, thus adversely affecting the performance of the cell and/or the capacity of the cell. In addition, the anolyte is chemically stable against the negative electrode active material.

In one embodiment of the invention, the negative electrode assembly has a thin film or foil as the negative electrode active material (as shown in FIG. 1e), and the dry polymer anolyte has a high modulus in order to prevent dendrite growth from the film during cell cycling. The thin film or foil may be lithium or lithium alloy, though other metal chemistries are possible, such as sodium or magnesium. Non-lithium metals and non-lithium metal alloys would be used with corresponding electrolyte salts that include the same metal as the electrochemically active metal in the negative electrode and with appropriate active materials in the cathode that can absorb and release the same metal ions. Graphite may also be used in combination with lithium salts and lithium-based active materials in the anode for secondary cells. The dry polymer anolyte also has good adhesion to the film or foil to ensure easy charge transfer and low interfacial impedance between the layers. In one arrangement, the dry polymer anolyte is void free. The dry polymer anolyte is electrochemically stable down to the lowest operating potential of the electrode. For example, with Li—Al planar electrodes, the NE dry polymer electrolyte is stable down to 0.3 V vs Li/Li$^+$. See Table 2 for other NE active materials and their associated potentials. In one arrangement, the dry polymer anolyte is mechanically rigid enough to prevent continuous reactivity of active material particles that undergo large volume changes during cell cycling by keeping them in electrical contact with the matrix of the composite electrode. When negative electrode active materials that undergo large volume expansion upon absorption of lithium are used as thin film electrodes, it is useful if the dry polymer anolyte has high yield strain to prevent electrode fatigue.

In another embodiment of the invention, the negative electrode active material is an alloy (examples of which are shown in Table 1) and has the form of particles. In order to prevent continuous reactivity, it is useful if the anolyte is electrochemically stable down to the reduction potentials shown. Additionally, it is useful if the anolyte has high impact toughness in order to maintain mechanical integrity and high yield strain in order to accommodate the volume change of the NE active material particles as they absorb and release lithium. It is also useful if the anolyte contains voids that can shrink to accommodate expansion. Good compatibility between the electrolyte and the particle surfaces helps to ensure good adhesion and homogeneous dispersion.

Finally, if a current collector is used, it is useful if the anolyte can adhere to the current collector.

TABLE 1

Negative Electrode Active Material Characteristics

| Negative Electrode Active Material | Reduction Potential vs. Li/Li+ (volts) | Maximum Volumetric Expansion |
|---|---|---|
| Li-Si | 0.4 | 30%-400% |
| Li-Al | 0.3 | 30%-400% |
| Li-Sn | 0.5 | 30%-450% |
| graphite | 0.2 | ~25% |

The negative electrode active material can be any of a variety of materials depending on the type of chemistry for which the cell is designed. In one embodiment of the invention, the cell is a lithium or lithium ion cell. The negative electrode material can be any material that can serve as a host material for (i.e., can absorb and release) lithium ions. Examples of such materials include, but are not limited to graphite, lithium metal, and lithium alloys such as Li—Al, Li—Si, Li—Sn, and Li—Mg. In one embodiment of the invention, a lithium alloy that contains no more than about 0.5 weight % aluminum is used. Silicon and silicon alloys are known to be useful as negative electrode materials in lithium cells. Examples include silicon alloys of tin (Sn), nickel (Ni), copper (Cu), iron (Fe), cobalt (Co), manganese (Mn), zinc (Zn), indium (In), silver (Ag), titanium (Ti), germanium (Ge), bismuth (Bi), antimony (Sb), and chromium (Cr) and mixtures thereof. In some arrangements, graphite, metal oxides, silicon oxides or silicon carbides can also be used as negative electrode materials.

Figure 2:
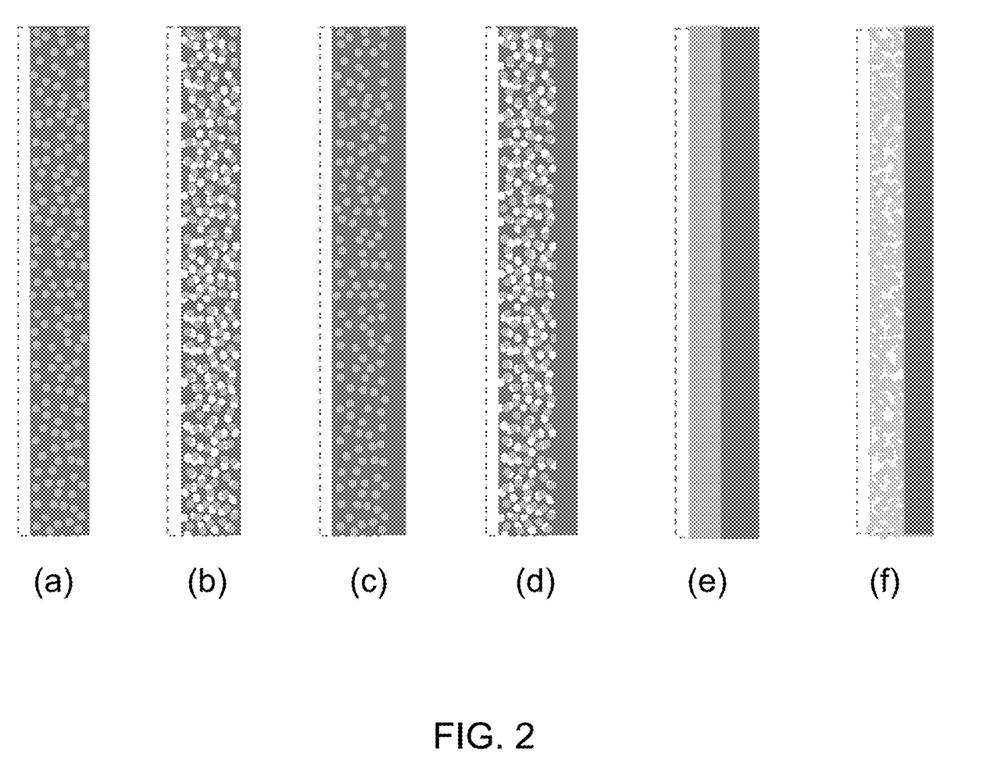

In one embodiment of the invention, a positive electrode assembly contains at least positive electrode active material and an electrolyte that has been chosen specifically for use with the positive electrode active material, referred to herein as a PE (positive electrode) electrolyte. FIG. 2 illustrates various exemplary arrangements for the positive electrode active material (light grey regions) and the catholyte (dark grey regions). The positive electrode active material can be arranged as particles (FIGS. 2a-2d) or as a thin film or foil (FIG. 2e). In some arrangements, the particles held together by a binder such as PVDF (polyvinyl difluoride), to form an open network or matrix that can be filled with liquid electrolyte. In some arrangements, the positive electrode assembly is formed by combining the positive electrode material particles with the catholyte to form a composite layer (FIGS. 2a-2d). In some arrangements, other materials (not shown) can be added to the composite layer to enhance, for example, electronic conduction. In some arrangements, the composite is porous, i.e., contains voids, which are shown as white spaces in FIGS. 2b, 2d; in other arrangements, it is pore-free (FIGS. 2a, 2c). In yet other arrangements (not shown), the catholyte of FIGS. 2e and 2f can also contain pores (not shown). In a positive electrode assembly that has a composite layer, the catholyte may be contained entirely within the composite layer (FIGS. 2a, 2b). In another arrangement, there can be a thin layer of additional catholyte adjacent the composite layer (FIGS. 2c, 2d). In some arrangements, a current collector (shown as a white layer defined by dashed lines) is also part of the positive electrode assembly.

In arrangements where the positive electrode active material is a thin film or foil, the positive electrode assembly contains at least the thin film or foil and a layer of the catholyte adjacent and in ionic contact with the thin film or foil as shown in FIG. 2e. In some arrangements, the positive electrode material is not a solid thin film, but instead is arranged as an aggregation of positive electrode active material particles close together to ensure ionic and electronic communication among the particles (FIG. 2f). Such a structure can be made, for example, by pressing and/or by sintering the positive electrode active material particles. In some arrangements, other materials such as carbon particles can be added to the layer of positive electrode material particles, for example, to enhance electronic or ionic conductivity. The positive electrode assembly contains at least the catholyte layer in ionic communication with the layer of positive electrode active material particles. In some arrangements there is also a current collector (shown as a white layer defined by dashed lines) in electronic contact with the positive electrode.

The catholyte is chosen specifically for use with the positive electrode active material. In one embodiment of the invention, the catholyte is a fluorinated ionic liquid catholyte that is oxidatively stable against the positive electrode active material. That is to say that the catholyte is resistant to continuous chemical and electrochemical reactions which would cause the catholyte to be oxidized at its interface with the positive electrode material. The catholyte is resistant to oxidation reactions over the range of potentials that the electrochemical cell experiences under conditions of storage and cycling. Such oxidation reactions at the positive electrode would increase cell impedance, thus adversely affecting the performance of the cell and/or the capacity of the cell. In addition, the catholyte is chemically stable against the positive electrode active material.

The positive electrode active material can be any of a variety of materials depending on the type of chemistry for which the cell is designed. In one embodiment of the invention, the cell is a lithium or lithium ion cell. The positive electrode active material can be any material that can serve as a host material for lithium ions. Examples of such materials include, but are not limited to materials described by the general formula $Li_xA_{1-y}M_yO_2$, wherein A comprises at least one transition metal selected from the group consisting of Mn, Co, and Ni; M comprises at least one element selected from the group consisting of B, Mg, Ca, Sr, Ba, Ti, V, Cr, Mn, Fe, Co, Ni, Cu, Al, In, Nb, Mo, W, Y, and Rh; x is described by $0.05 \leq x \leq 1.1$; and y is described by $0 \leq y \leq 0.5$. In one arrangement, the positive electrode material is $LiNi_{0.5}Mn_{0.5}O_2$.

In one arrangement, the positive electrode active material is described by the general formula: $Li_xMn_{2-y}M_yO_2$, where M is chosen from Mn, Ni, Co, and/or Cr; x is described by $0.05 \leq x \leq 1.1$; and y is described by $0 \leq y \leq 2$. In another arrangement, the positive electrode active material is described by the general formula: $Li_xM_yMn_{4-y}O_8$, where M is chosen from Fe and/or Co; x is described by $0.05 \leq x \leq 2$; and y is described by $0 \leq y \leq 4$. In another arrangement, the positive electrode active material is given by the formula $Li_x(Fe_yM_{1-y})PO_4$, where M is chosen from transition metals such as Mn, Co and/or Ni; x is described by $0.9 \leq x \leq 1.1$; and y is described by $0 \leq y \leq 1$. In yet another arrangement, the positive electrode active material is given by the general formula: $Li(Ni_{0.5-x}Co_{0.5-x}M_{2x})O_2$, where M is chosen from Al, Mg, Mn, and/or Ti; and x is described by $0 \leq x \leq 0.2$. In some arrangements, the positive electrode material includes $LiNiVO_2$.

Examples of appropriate positive electrode active materials also include compounds such as, $FeS_2$, FeOF, $FeF_3$, $FeF_2$, $MoO_3$, sulfur, lithium polysulfides, CuO, $Cu_2O$, FeO, $Fe_2O_3$, $V_6O_{13}$, $VO_2$, $Li_{1+x}V_3O_8$ ($0 \leq x \leq 3$), $Ag_xV_2O_5$ ($0 \leq x \leq 2$), $Cu_xV_4O_{11}$ ($0 \leq x \leq 3$), $VOPO_4$, $LiCoO_2$, lithium iron phosphate (LFP), nickel-cobalt manganese (NCM), nickel cobalt aluminum (NCA), or mixtures thereof.

Most electrolytes exhibit electrochemical stability over a limited window of about 4 Volts. Thus, a single electrolyte cannot by itself support an electrochemical couple that has a voltage between electrodes higher than 4 Volts. Yet such high voltage electrochemical cells can be made to be stable and robust using the structures and materials described herein. Two different electrolytes—a anolyte that is reductively stable at the anode (but may or may not be oxidatively stable at the cathode) and a catholyte that is oxidatively stable at the cathode (but may or may not be reductively stable at the anode) can now be used in the same electrochemical cell. In one embodiment of the invention, the anolyte is optimized for reductive stability and the catholyte is optimized for oxidative stability. By allowing different electrolytes to be used at the negative electrode and at the positive electrode, each electrode can be designed for optimum performance without compromise. Such an arrangement is especially useful and for high voltage applications.

There have been efforts in recent years to develop high voltage (i.e., greater than ~4.2V) electrochemical cells by using "high voltage cathode materials" such as those listed in Table 2.

TABLE 2

Positive Electrode Active Material Characteristics

| Positive Electrode Active Material | Discharge Potential vs. Li/Li+ (volts) | Typical Charging cut off Potential Li/Li+ (volts) |
| --- | --- | --- |
| $LiFePO_4$ | 3.4 | 3.8 |
| $LiCoO_2$ | 3.6 | 4.2 |
| $LiMnPO_4$ | 4.1 | 4.3 |
| $LiAl_{0.05}Co_{0.15}Ni_{0.8}O_2$ | 3.6 | 4.3 |
| $LiCoPO_4$ | 4.8 | 5.0 |
| $LiNiPO_4$ | 5.1 | 5.4 |
| $Li_{1.07}Mn_{1.93}O_4$ | 3.9 | 4.3 |

Unfortunately, electrolytes that are stable to oxidation at the high potentials at the cathode/electrolyte interface are not generally stable to reduction at the lower potentials at the anode/electrolyte interface for standard anode materials. Now an electrochemical cell that uses different, specifically chosen electrolytes, some of which may be dry polymer electrolytes, at the cathode and at the anode sides of the cell, as described herein, can overcome this problem and make it possible to design and build high voltage cells.

Lithium metal and alloy negative electrode active materials are particularly prone to ongoing reduction reactions with many conventional lithium-ion electrolytes, as these negative electrode active materials tend not to form stable passivation layers. Although some electrolytes may be able to form stable interfaces with such anode materials, such electrolytes may not work well in the rest of the cell or in the positive electrode assembly due to limitations in conductivity and/or oxidative stability. Electrochemical cells that can use different electrolytes specifically chosen for their compatibility with each electrode, as described in the embodiments herein, can overcome these limitations.

The embodiments of the invention, as described above, can result in an electrochemical cell with very good performance. In one embodiment of the invention, such a cell has a Li cycling efficiency greater than 99.7%, over 500 cycles. In another embodiment of the invention, such a cell has a Li cycling efficiency of greater than 99.9%, over 500 cycles. In another embodiment of the invention, there is very little impedance increase at the negative electrode, the positive electrode, or at both electrodes as the cell is cycled. In one arrangement, the impedance value at 500 cycles increases by no more than 40% from the impedance value at 10 cycles. In another arrangement, the impedance value at 500 cycles increases by no more than 20% from the impedance value at 10 cycles. In yet another arrangement, the impedance value at 500 cycles increases by no more than 10% from the impedance value at 10 cycles. In one embodiment of the invention, the capacity of the electrolyte cell at 500 cycles decreases by no more than 40% from the capacity at 10 cycles. In another embodiment of the invention, the capacity of the electrolyte cell at 500 cycles decreases by no more than 20% from the capacity at 10 cycles. In yet another embodiment of the invention, the capacity of the electrolyte cell at 500 cycles decreases by no more than 10% from the capacity at 10 cycles. In yet another embodiment of the invention, the capacity of the electrolyte cell at 500 cycles decreases by no more than 5% from the capacity at 10 cycles.

When negative and positive electrode assemblies are each optimized independently, not only is it possible to optimize electrochemical stability, but it also presents the opportunity to overcome other key limitations that may be specific to individual electrode active materials.

For example, some negative electrode active materials undergo a large volume increase, as much as 300% or more, upon lithiation. Some examples are shown above in Table 2. For composite negative electrode assemblies that contain voids such as the electrode assemblies in FIGS. 1b, 1d, it is possible to accommodate volumetric expansion and contraction of the negative electrode active material upon cycling. It is useful if the anolyte is a dry polymer electrolyte that has a yield strain greater than or equal to the maximum volume expansion of the negative electrode material. In this way, the anolyte is elastic enough to move into the void space as the negative electrode active material expands. It is also useful if the total void space is at least as large as the maximum total volume expansion of the negative electrode active material. In other arrangements, the negative electrode material particles are shaped into a porous layer adjacent the anolyte layer to form the negative electrode assembly as shown in FIG. 1f. The pores in the layer can accommodate expansion of the negative electrode active material. Further details about porous electrodes can be found in U.S. Pat. No. 9,054,372, issued Jun. 9, 2015, which is included by reference herein.

In general, cathode active materials expand and contract much less during cell cycling than do anode active materials. Thus, there are different mechanical considerations when choosing an electrolyte for a cathode rather than for an anode, and it may be desirable to choose different electrolytes for these two regions of an electrochemical cell. For example, if the positive electrode active material expands and contracts much less than the negative electrode active material, it may be optimal to employ an electrolyte that is less elastic for the cathode region of the cell or to create an electrode assembly for the cathode that does not include voids, thereby optimizing other key parameters in the cathode assembly such as mechanical robustness or energy density.

For positive electrode active materials that contain transition metals, dissolution of these metals into a standard liquid electrolyte upon cycling can be a serious problem, especially in high voltage cells and at high temperatures. The dissolution can cause accelerated cell degradation or premature failure. Examples of possible failure mechanisms include:
  a) the composition of the positive electrode active materials changes as the metals dissolve, adversely impacting the ability of the active material to absorb and release lithium,
  b) the dissolved metals can diffuse to the negative electrode and degrade the capacity of the negative electrode active material,
  c) the dissolved metals can diffuse to the negative electrode and degrade any passivation layer on the negative electrode active material, resulting in continual electrolyte reaction with the negative electrode active material, and
  d) the dissolved metals can create internal shorts or other defects within the cell.

For example, in the case of $Mn_2O_4$ positive electrode active material, it is useful if the electrolyte does not dissolve the electrochemically active manganese. In the case of a sulfur cathode, it is useful if the electrolyte does not dissolve the electrochemically active sulfur or polysulfide. In one arrangement, less than 10% of the electrochemically active ion dissolves from the positive electrode active material after 500 cycles in the temperature range 45-80° C. In another arrangement, less than 5% of the electrochemically active ion dissolves from the positive electrode active material after 500 cycles in the temperature range 45-80° C. In yet another arrangement, less than 1% of the electrochemically active ion dissolves from the positive electrode active material after 500 cycles in the temperature range 45-80° C. This allows for selection of a separate non-dissolving electrolyte on the cathode side and can prevent diffusion of metal to the anode. A positive electrode assembly can be optimized to prevent dissolution, for example, employing a ceramic or solid polymer electrolyte as the catholyte. Although dissolution of electrochemically active ions may not be an issue for the negative electrode assembly, other considerations may be important, such as high ionic conductivity or reductively stability, and it may be possible that a different electrolyte would be preferred.

In one embodiment of the invention, the anolyte is a solid electrolyte. In one arrangement, the anolyte is a ceramic electrolyte. In another arrangement, the anolyte is a dry polymer electrolyte. In yet another arrangement, the anolyte is a dry block copolymer electrolyte.

In one embodiment of the invention, the anolyte is a liquid electrolyte or a gel containing a liquid electrolyte. When a liquid electrolyte is used, it is most useful if the liquid electrolyte is immiscible with electrolytes in adjacent regions of the cell or if a selectively permeable membrane is positioned to prevent mixing of the liquid electrolyte with the electrolyte in the separator. Such a membrane allows electrochemical cations to move through, but not the liquid itself. In the absence of containment by such a membrane, miscible liquids can diffuse easily throughout the cell. If such diffusion were to occur, the benefits provided by using different electrolytes in different regions of the cell may be diminished or negated. In the worst case, active materials in the electrodes could be oxidized or reduced, seriously compromising the performance and/or the life of the cell.

In one embodiment of the invention, the catholyte is a fluorinated ionic liquid electrolyte or a gel containing a fluorinated ionic liquid electrolyte. When a fluorinated ionic liquid electrolyte is used, it is most useful if the fluorinated ionic liquid electrolyte is immiscible with electrolytes in adjacent regions of the cell or if a selectively permeable membrane is positioned to prevent mixing of the fluorinated ionic liquid electrolyte with the electrolyte in the separator. Such a membrane allows electrochemical cations to move through, but not the liquid itself. In the absence of containment by such a membrane, miscible liquids can diffuse easily throughout the cell. If such diffusion were to occur, the benefits provided by using different electrolytes in different regions of the cell may be diminished or negated. In the worst case, active materials in the electrodes could be oxidized or reduced, seriously compromising the performance and/or the life of the cell.

In one embodiment of the invention, a separator electrolyte is used between the negative electrode assembly and the positive electrode assembly. In one embodiment of the invention, the separator electrolyte can be the same as the anolyte. In another embodiment, the separator electrolyte is different from both the anolyte and the catholyte. The separator electrolyte can be any of liquid electrolytes, solid electrolytes, ceramic electrolytes, polymer electrolytes, dry polymer electrolytes, and block copolymer electrolytes, independent of the anolyte and the catholyte. In some arrangements, the electrolytes are chosen so that no two liquid electrolytes are adjacent one another. When a liquid electrolyte is used, it is most useful if the liquid electrolyte is immiscible with electrolytes in adjacent regions of the cell or if a selective membrane is positioned at each interface to prevent mixing of the liquid electrolyte with adjacent electrolytes. Such a membrane allows electrochemical cations to move through but not the liquid itself. In the absence of containment, miscible liquids can diffuse easily throughout the cell. If such diffusion were to occur, the benefits provided by using different electrolytes in different regions of the cell may be diminished or negated. In the worst case, such diffusion could cause reduction at the negative electrode assembly and/or oxidation at the positive electrode assembly, causing premature failure of the cell.

In general, it is useful if the separator electrolyte has enough mechanical integrity to ensure that the negative electrode assembly and the positive electrode assembly do not come into physical contact with one another. In some arrangements, when a liquid, gel, or soft polymer is used as the separator electrolyte, a separator membrane is used with it.

It is useful if any two electrolytes meeting at an interface are immiscible in each other and chemically compatible with each other. It is also useful if there is little or no impedance or concentration overpotential across the interface.

In one arrangement, all electrolytes are stable over the range of storage and operating temperatures and the range of operating potentials for the electrochemical cell. Using the embodiments described here, this condition can be met for electrode couples that are otherwise unstable with conventional electrolytes or in conventional single-electrolyte architectures.

Figure 3:
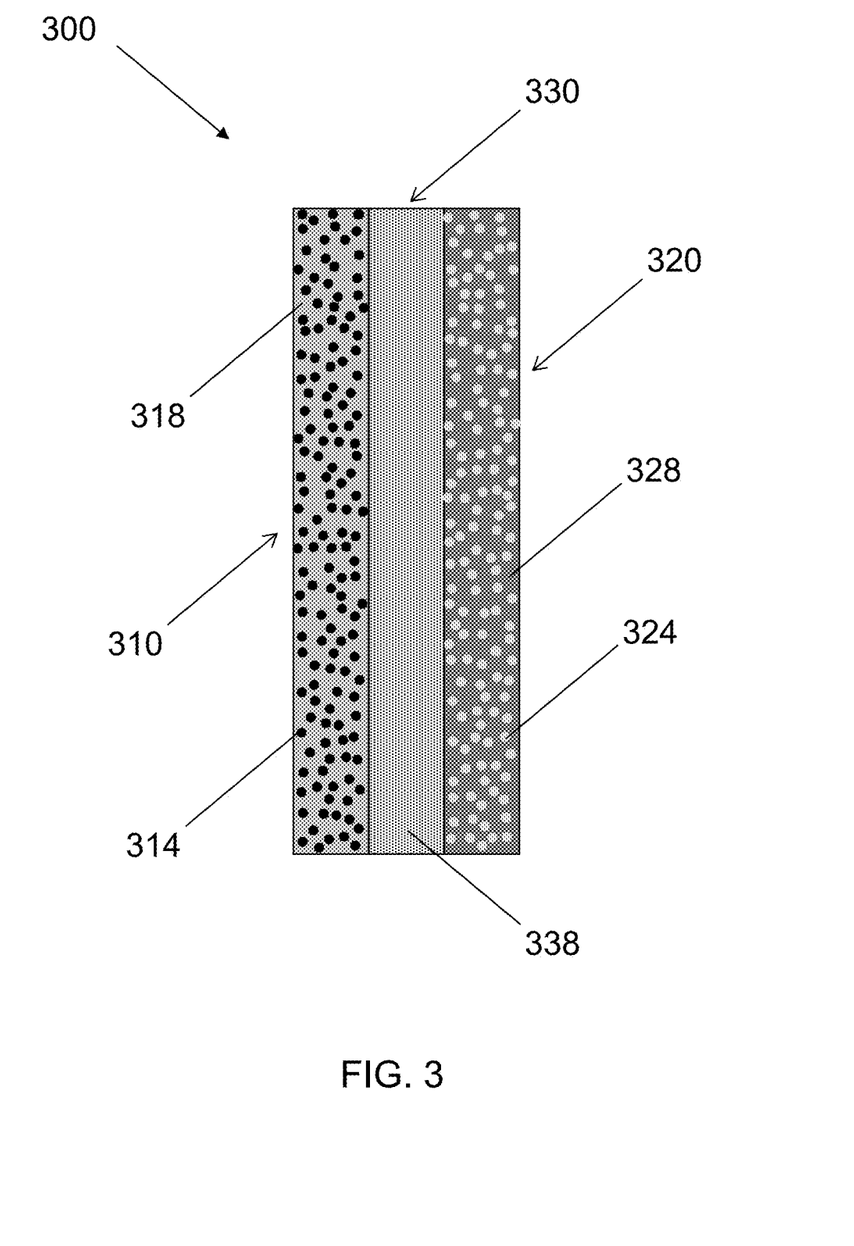
FIG. 3 is a schematic illustration of an electrochemical cell, according to an embodiment of the invention.

FIG. 3 is a schematic cross section that shows an electrochemical cell in an exemplary embodiment of the invention. The cell 300 has a negative electrode assembly 310, a positive electrode assembly 320, with an intervening separator 330. The exemplary negative electrode assembly 310 is the same as the one shown in FIG. 1a. The negative electrode assembly 310 is an aggregation of negative electrode active material particles 314 dispersed within a NE dry polymer electrolyte 318. There can also be electronically-conducting particles such as carbon particles (not shown) in the negative electrode assembly 310. The exemplary positive electrode assembly 320 is the same as the one shown in FIG. 2a. The positive electrode assembly 320 is an aggregation of positive electrode active material particles 324 dispersed within a fluorinated ionic liquid catholyte 328. In some arrangements, the positive electrode active material particles 324 are held together by a binder such as PVDF (polyvinyl difluoride), to form an open network or matrix that can be filled with the PE fluorinated ionic liquid electrolyte 328. There can also be electronically-conducting particles such as carbon particles (not shown) in the positive electrode assembly 320. In other exemplary embodiments, other electrode assembly configurations, such as those shown in FIGS. 1 and 2, can be substituted in the electrochemical cell shown in FIG. 3.

The anolyte 318 and the catholyte 328 are each optimized for their respective electrodes as has been discussed above. In one arrangement, the anolyte 318 and the catholyte 328 are different. The separator 330 contains a separator electrolyte 338, which is also optimized for its role in the cell 300. In one arrangement, the separator electrolyte 338 is immiscible with both the anolyte 318 and the catholyte 328. In another arrangement, the separator electrolyte 338 is miscible with either or both of the anolyte 318 and the catholyte 328, and selectively permeable membranes (not shown) are positioned at interfaces between the miscible electrolytes. In one arrangement, the separator electrolyte 338 is the same as the anolyte 318. In another arrangement, the separator electrolyte 338 is different from both the anolyte 318 and the catholyte 328.

In one arrangement, the anolyte 318 and the separator electrolyte 338 are both solid electrolytes. In some arrangements, solid electrolytes can be made of ceramic materials or polymer materials. In one arrangement, solid electrolytes can be made of dry polymer materials. In one arrangement, the solid electrolytes are block copolymer electrolytes. In some arrangements, one or more of the anolyte 318, the catholyte 328, and the separator electrolyte 338 is a liquid. When a liquid electrolyte is used, care must be taken to ensure that the liquid cannot diffuse out of its own functional region (i.e., negative electrode assembly, positive electrode assembly, or separator) into other functional regions of the cell. In some arrangements, a selectively permeable membrane is used at any interface where at least one electrolyte is liquid. In other arrangements, the liquid electrolytes that are used are immiscible with any adjacent electrolyte.

Figure 4:
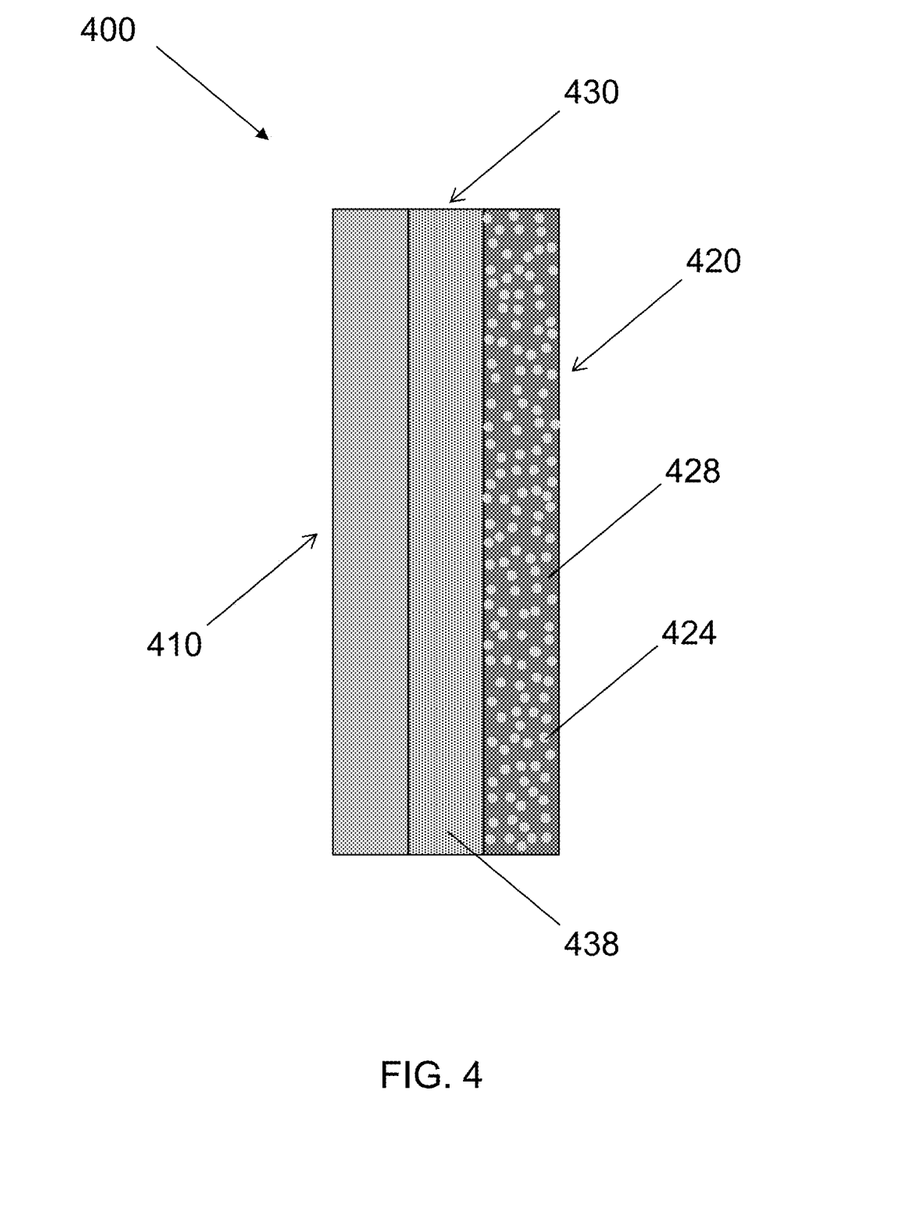
FIG. 4 is a schematic illustration of an electrochemical cell, according to another embodiment of the invention.

FIG. 4 is a schematic cross section that shows an electrochemical cell in another exemplary embodiment of the invention. The cell 400 has a negative electrode 410, a positive electrode assembly 420, with an intervening separator 430. The exemplary negative electrode 410 is a lithium metal or lithium metal alloy foil. The exemplary positive electrode assembly 420 is an aggregation of positive electrode active material particles 424 held together by a binder (not shown) such as one or more of PVDF (polyvinylidene fluoride), P(VDF-HFP) (poly(vinylidenefluoride-hexafluoropropylene), P(VDF-CTFE) (poly(vinylidene fluoride-chlorotrifluoroethylene)), carboxymethylcellulose, and styrene-butadiene rubber, and surrounded by a fluorinated ionic liquid electrolyte 428. There can also be electronically-conducting particles such as carbon particles (not shown) in the positive electrode assembly 420. The electronically-conducting particles may be acetylene black, vapor-grown carbon fiber, or graphite powder, and are present in sufficient quantity to allow electronic conduction throughout the cathode.

The separator 430 contains a separator electrolyte 438, which is immiscible with the catholyte 428. In another arrangement, the separator electrolyte 438 is miscible with the catholyte 428, and a selectively permeable membrane (not shown) is positioned at the interface between the miscible electrolytes. In one arrangement, the separator electrolyte 438 is a block copolymer electrolyte as discussed above. In one arrangement, the separator electrolyte 438 is a diblock or triblock copolymer wherein one block is poly(ethylene oxide) to provide ionic conduction and the other block is poly(styrene) or other physically robust polymer providing structural support. In some arrangements, the separator electrolyte 438 is made of ceramic materials or polymer materials. In one arrangement, the separator electrolyte 438 can be made of dry polymer materials. In one arrangement, the solid electrolytes are block copolymer electrolytes. In some arrangements, the separator electrolyte 438 is a liquid. When a liquid electrolyte is used, care must be taken to ensure that the liquid cannot diffuse out of the separator region into other functional regions of the cell. In some arrangements, a selectively permeable membrane is used at any interface where at least one electrolyte is liquid. In other arrangements, the liquid electrolytes that are used are immiscible with any adjacent electrolyte.

The metal salt in the separator is typically a lithium salt with a weakly coordinating anion, such as LiTFSI, LiFSI, LiPF$_6$, LiFAP, LiBF4, LiClO$_4$, LiOTf, LiC(Tf)$_3$, LiBOB, LiDFOB, LiB(CN)$_4$ among others.

The active material in the cathode is selected from the lithium metal oxides or lithium metal phosphates typically used for lithium batteries. It may be possible to use conversion electrodes such as elemental sulfur, or sulfur composites with carbon or ionically-conductive polymer.

The metal salt in the cathode is typically identical to one or more of the salts present in the block copolymer separator. A fluorinated counter-ion is more likely to be soluble at useful levels in the fluorinated liquid such as many of the salts listed above.

Electrolytes that can be Used in the Embodiments of the Invention

Ceramic Electrolytes

Examples of ceramic electrolytes that can be used in the embodiments of the invention include lithium silicate, lithium borate, lithium aluminate, lithium phosphate, lithium phosphorus oxynitride, lithium silicosulfide, lithium borosulfide, lithium aluminosulfide, and lithium phosphosulfide. Other examples include lithium lanthanum titanium oxide, lithium lanthanum zirconium oxide, LiPON, LiSICON, Li$_{10}$SnP$_2$S$_{12}$, Li$_{11}$Si$_2$PS$_{12}$, Li$_{10}$GeP$_2$S$_{12}$, Li$_2$S—SiS$_2$—Li$_3$PO$_4$, Li$_{14}$Zn(GeO$_4$)$_4$, Li$_2$S—P$_2$S$_5$, La$_{0.5}$Li$_{0.5}$TiO$_3$, combinations thereof, and others known in the field.

Polymer Electrolytes

There are a variety of polymer electrolytes that are appropriate for use in the inventive structures described herein. In one embodiment of the invention, an electrolyte contains one or more of the following optionally cross-linked polymers: polyethylene oxide, polysulfone, polyacrylonitrile, siloxane, polyether, polyamine, linear copolymers containing ethers or amines, ethylene carbonate, Nafion®, and polysiloxane grafted with small molecules or oligomers that include polyethers and/or alkylcarbonates.

In one embodiment of the invention, the solid polymer electrolyte, when combined with an appropriate salt, is chemically and thermally stable and has an ionic conductivity of at least $10^{-5}$ Scm$^{-1}$ at a desired operating temperature. In one arrangement, the polymer electrolyte has an ionic conductivity of at least $10^{-3}$ Scm$^{-1}$ at operating temperature. Examples of useful operating temperatures include room temperature (25° C.), and 80° C. Examples of appropriate salts for any electrolyte disclosed herein include, but are not limited to metal salts selected from the group consisting of chlorides, bromides, sulfates, nitrates, sulfides, hydrides, nitrides, phosphides, sulfonamides, triflates, thiocynates, perchlorates, borates, or selenides of lithium, sodium, potassium, silver, barium, lead, calcium, ruthenium, tantalum, rhodium, iridium, cobalt, nickel, molybdenum, tungsten or vanadium. Alkali metal salts such as lithium salts, sodium salts, potassium salts, and cesium salts can be used. Examples of specific lithium salts include LiSCN, LiN(CN)$_2$, LiClO$_4$, LiBF$_4$, LiAsF$_6$, LiPF$_6$, LiCF$_3$SO$_3$, Li(CF$_3$SO$_2$)$_2$N, Li(CF$_3$SO$_2$)$_3$C, LiN(SO$_2$C$_2$F$_5$)$_2$, LiN(SO2F)$_2$, LiN(SO$_2$CF$_3$)$_2$, LiN(SO$_2$CF$_2$CF$_3$)$_2$, lithium alkyl fluorophosphates, lithium oxalatoborate, as well as other lithium bis(chelato)borates having five to seven membered rings, LiPF$_3$(C$_2$F$_5$)$_3$, LiPF$_3$(CF$_3$)$_3$, LiB(C$_2$O$_4$)$_2$, LiOTf, LiC(Tf)3, LiDFOB, LiTCB and mixtures thereof. In other embodiments of the invention, for other electrochemistries, electrolytes are made by combining the polymers with various kinds of salts. Examples include, but are not limited to AgSO$_3$CF$_3$, NaSCN, NaSO$_3$CF$_3$, KTFSI, NaTFSI, Ba(TFSI)$_2$, Pb(TFSI)$_2$, and Ca(TFSI)$_2$. Concentration of metal salts in the electrolytes disclosed herein range from 5 to 50 wt %, 5 to 30 wt %, 10 to 20 wt %, or any range subsumed therein. As described in detail above, a block copolymer electrolyte can be used in the embodiments of the invention.

Block Copolymer Electrolytes

Figure 5A:
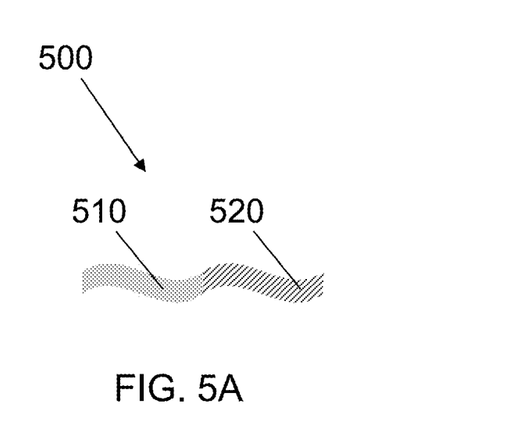
FIG. 5A is a simplified illustration of an exemplary diblock polymer molecule.

FIG. 5A is a simplified illustration of an exemplary diblock polymer molecule 500 that has a first polymer block 510 and a second polymer block 520 covalently bonded together. In one arrangement both the first polymer block 510 and the second polymer block 520 are linear polymer blocks. In another arrangement, either one or both polymer blocks 510, 520 has a comb structure. In one arrangement, neither polymer block is cross-linked. In another arrangement, one polymer block is cross-linked. In yet another arrangement, both polymer blocks are cross-linked.

Figure 5B:
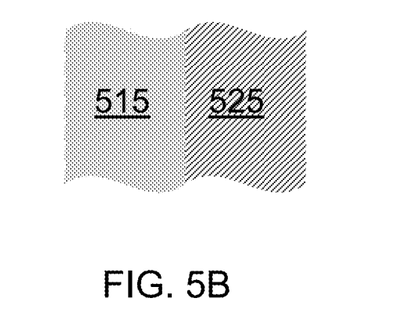
FIG. 5B is a simplified illustration of multiple diblock polymer molecules as shown in FIG. 5A arranged to form a domain structure.
Figure 5C:
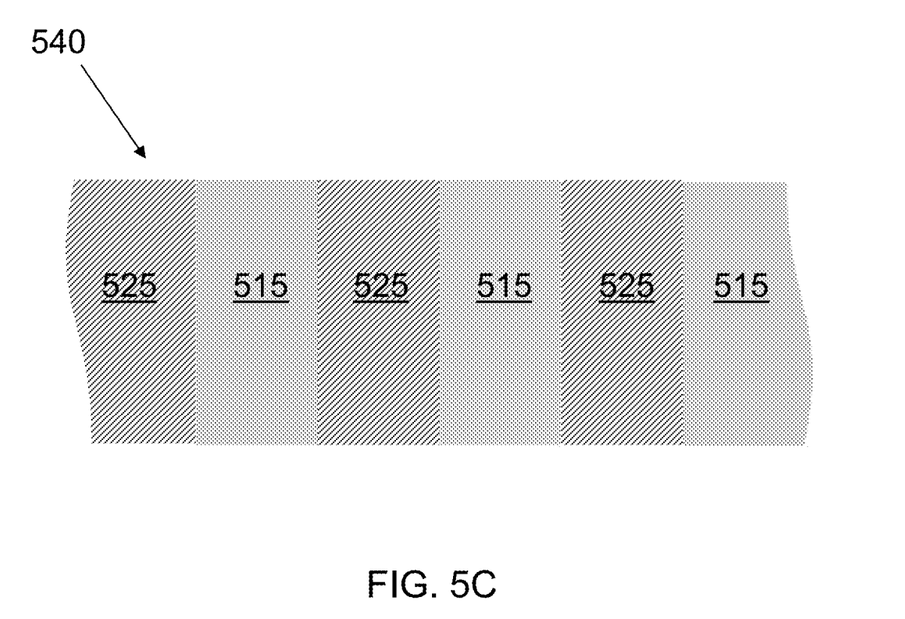
FIG. 5C is a simplified illustration of multiple domain structures as shown in FIG. 5B arranged to form multiple repeat domains, thereby forming a continuous nanostructured block copolymer material.

Multiple diblock polymer molecules 500 can arrange themselves to form a first domain 515 of a first phase made of the first polymer blocks 510 and a second domain 525 of a second phase made of the second polymer blocks 520, as shown in FIG. 5B. Diblock polymer molecules 500 can arrange themselves to form multiple repeat domains, thereby forming a continuous nanostructured block copolymer material 540, as shown in FIG. 5C. The sizes or widths of the domains can be adjusted by adjusting the molecular weights of each of the polymer blocks.

In one arrangement the first polymer domain 515 is ionically conductive, and the second polymer domain 525 provides mechanical strength to the nanostructured block copolymer.

Figure 6A:
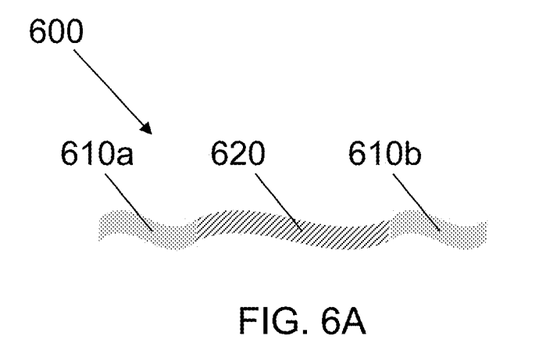
FIG. 6A is a simplified illustration of an exemplary triblock polymer molecule, wherein two blocks are the same.

FIG. 6A is a simplified illustration of an exemplary triblock polymer molecule 600 that has a first polymer block 610*a*, a second polymer block 620, and a third polymer block 610*b* that is the same as the first polymer block 610*a*, all covalently bonded together. In one arrangement the first polymer block 610*a*, the second polymer block 620, and the third copolymer block 610*b* are linear polymer blocks. In another arrangement, either some or all polymer blocks 610*a*, 620, 610*b* have a comb structure. In one arrangement, no polymer block is cross-linked. In another arrangement, one polymer block is cross-linked. In yet another arrangement, two polymer blocks are cross-linked. In yet another arrangement, all polymer blocks are cross-linked.

Figure 6B:
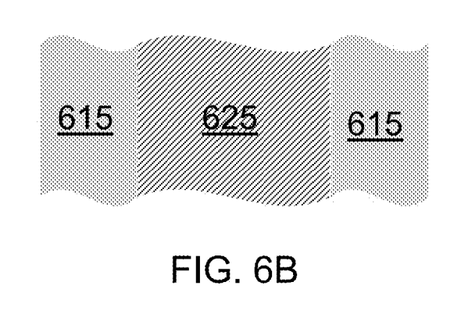
FIG. 6B is a simplified illustration of multiple triblock polymer molecules as shown in FIG. 6A arranged to form a domain structure.
Figure 6C:
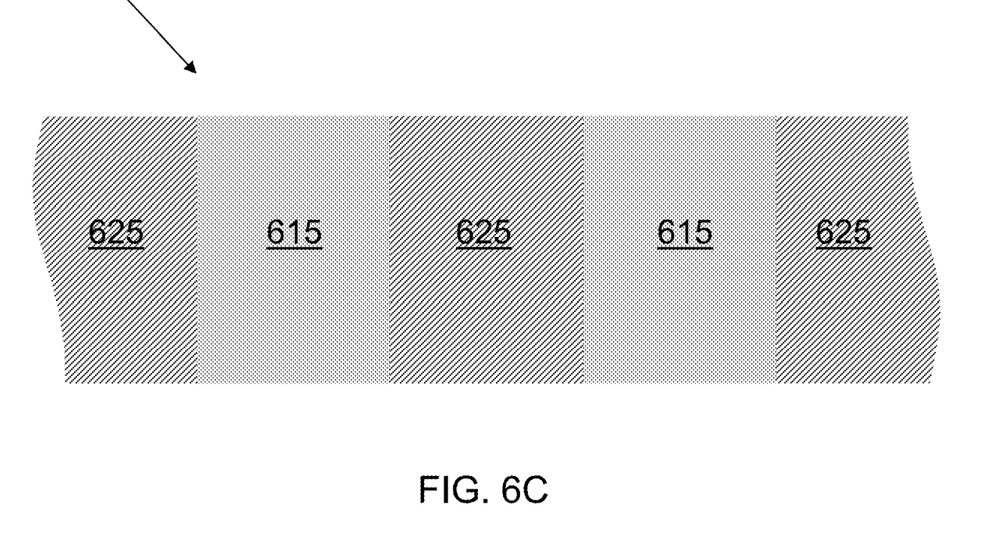
FIG. 6C is a simplified illustration of multiple domain structures as shown in FIG. 6B arranged to form multiple repeat domains, thereby forming a continuous nanostructured block copolymer material.

Multiple triblock polymer molecules 600 can arrange themselves to form a first domain 615 of a first phase made of the first polymer blocks 610a, a second domain 625 of a second phase made of the second polymer blocks 620, and a third domain 615b of a first phase made of the third polymer blocks 610b as shown in FIG. 6B. Triblock polymer molecules 600 can arrange themselves to form multiple repeat domains 625, 615 (containing both 615a and 615b), thereby forming a continuous nanostructured block copolymer 630, as shown in FIG. 6C. The sizes of the domains can be adjusted by adjusting the molecular weights of each of the polymer blocks.

In one arrangement the first and third polymer domains 615a, 615b are ionically conductive, and the second polymer domain 625 provides mechanical strength to the nanostructured block copolymer. In another arrangement, the second polymer domain 625 is ionically conductive, and the first and third polymer domains 615 provide a structural framework.

Figure 7A:
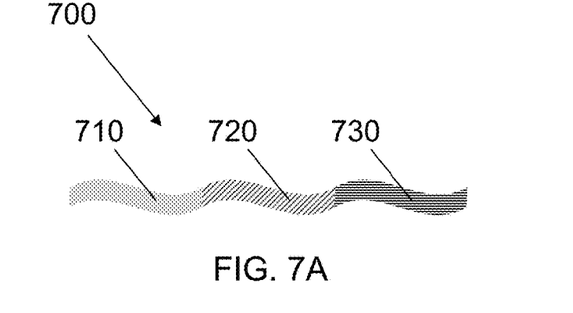
FIG. 7A is a simplified illustration of an exemplary triblock polymer molecule, wherein no two blocks are the same.

FIG. 7A is a simplified illustration of another exemplary triblock polymer molecule 700 that has a first polymer block 710, a second polymer block 720, and a third polymer block 730, different from either of the other two polymer blocks, all covalently bonded together. In one arrangement the first polymer block 710, the second polymer block 720, and the third copolymer block 730 are linear polymer blocks. In another arrangement, either some or all polymer blocks 710, 720, 730 have a comb structure. In one arrangement, no polymer block is cross-linked. In another arrangement, one polymer block is cross-linked. In yet another arrangement, two polymer blocks are cross-linked. In yet another arrangement, all polymer blocks are cross-linked.

Figure 7B:
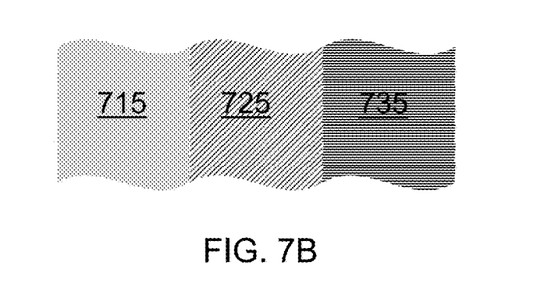
FIG. 7B is a simplified illustration of multiple triblock polymer molecules as shown in FIG. 7A arranged to form a domain structure.
Figure 7C:
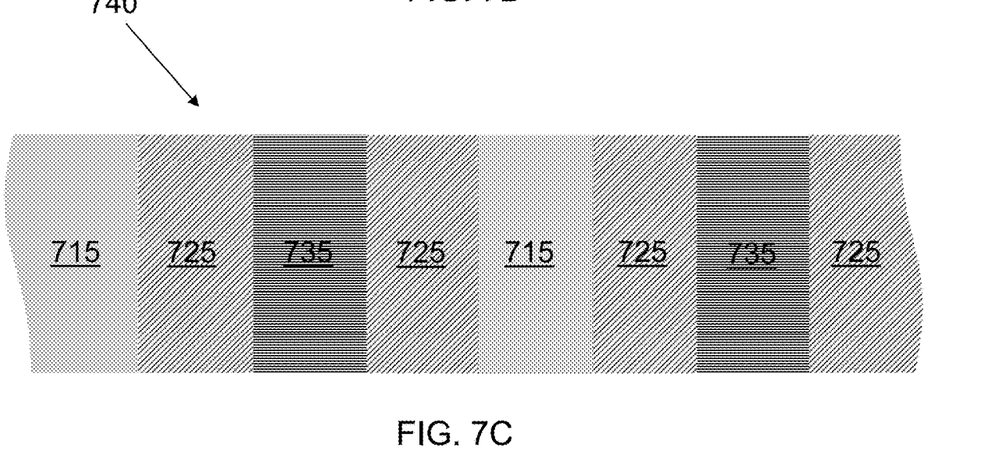
FIG. 7C is a simplified illustration of multiple domain structures as shown in FIG. 7B arranged to form multiple repeat domains, thereby forming a continuous nanostructured block copolymer material.

Multiple triblock polymer molecules 700 can arrange themselves to form a first domain 715 of a first phase made of the first polymer blocks 710a, a second domain 725 of a second phase made of the second polymer blocks 720, and a third domain 735 of a third phase made of the third polymer blocks 730 as shown in FIG. 7B. Triblock polymer molecules 700 can arrange themselves to form multiple repeat domains, thereby forming a continuous nanostructured block copolymer 740, as shown in FIG. 7C. The sizes of the domains can be adjusted by adjusting the molecular weights of each of the polymer blocks.

In one arrangement the first polymer domains 715 are ionically conductive, and the second polymer domains 725 provide mechanical strength to the nanostructured block copolymer. The third polymer domains 735 provides an additional functionality that may improve mechanical strength, ionic conductivity, chemical or electrochemical stability, may make the material easier to process, or may provide some other desirable property to the block copolymer. In other arrangements, the individual domains can exchange roles.

Choosing appropriate polymers for the block copolymers described above is important in order to achieve desired electrolyte properties. In one embodiment, the conductive polymer exhibits ionic conductivity of at least $10^{-5}$ Scm$^{-1}$ at electrochemical cell operating temperatures when combined with an appropriate salt(s), such as lithium salt(s); is chemically stable against such salt(s); and is thermally stable at electrochemical cell operating temperatures. In one embodiment, the structural material has a modulus in excess of $1 \times 10^5$ Pa at electrochemical cell operating temperatures. In one embodiment, the third polymer is rubbery; and has a glass transition temperature lower than operating and processing temperatures. It is useful if all materials are mutually immiscible.

In one embodiment of the invention, the conductive phase can be made of a linear polymer. Conductive linear polymers that can be used in the conductive phase include, but are not limited to, polyethers, polyamines, polyimides, polyamides, alkyl carbonates, polynitriles, polyesters, and combinations thereof. The conductive linear polymers can also be used in combination with polysiloxanes, polyphosphazines, polyolefins, and/or polydienes to form the conductive phase.

In another exemplary embodiment, the conductive phase is made of comb polymers that have a backbone and pendant groups. Backbones that can be used in these polymers include, but are not limited to, polysiloxanes, polyphosphazines, polyethers, polydienes, polyolefins, polyacrylates, polymethacrylates, and combinations thereof. Pendants that can be used include, but are not limited to, oligoethers, substituted oligoethers, nitrile groups, sulfones, thiols, polyethers, polyamines, polyimides, polyamides, alkyl carbonates, polynitriles, polyesters, other polar groups, single ion conducting groups, and combinations thereof.

There are no particular restrictions on the electrolyte salt that can be used in the block copolymer electrolytes. Any electrolyte salt that includes the ion identified as the most desirable charge carrier for the application can be used. It is especially useful to use electrolyte salts that have a large dissociation constant within the polymer electrolyte.

Suitable examples include alkali metal salts, such as Li salts. Examples of useful Li salts include, but are not limited to, LiPF$_6$, LiN(CF$_3$SO$_2$)$_2$, LiN(FSO$_2$)$_2$, Li(CF$_3$SO$_2$)$_3$C, LiN(SO$_2$CF$_2$CF$_3$)$_2$, LiB(C$_2$O$_4$)$_2$, Bi$_2$F$_x$H$_{12-x}$, B$_{12}$F$_{12}$, and mixtures thereof. Non-lithium salts such as salts of aluminum, sodium, and magnesium are examples of other salts that can be used.

In one embodiment of the invention, single ion conductors can be used with electrolyte salts or instead of electrolyte salts. Examples of single ion conductors include, but are not limited to sulfonamide salts, boron-based salts, and sulfates groups.

In one embodiment of the invention, the structural phase can be made of polymers such as polystyrene, hydrogenated polystyrene, polymethacrylate, poly(methyl methacrylate), polyvinylpyridine, polyvinylcyclohexane, polyimide, polyamide, polypropylene, polyolefins, poly(t-butyl vinyl ether), poly(cyclohexyl methacrylate), poly(cyclohexyl vinyl ether), poly(t-butyl vinyl ether), polyethylene, poly(phenylene oxide), poly(2,6-dimethyl-1,4-phenylene oxide) (PXE), poly(phenylene sulfide), poly(phenylene sulfide sulfone), poly(phenylene sulfide ketone), poly(phenylene sulfide amide), polysulfone, fluorocarbons, such as polyvinylidene fluoride, or copolymers that contain styrene, methacrylate, or vinylpyridine. It is especially useful if the structural phase is rigid and is in a glassy or crystalline state.

Additional species can be added to nanostructured block copolymer electrolytes to enhance the ionic conductivity, to enhance the mechanical properties, or to enhance any other properties that may be desirable.

The ionic conductivity of nanostructured block copolymer electrolyte materials can be improved by including one or more additives in the ionically conductive phase. An additive can improve ionic conductivity by lowering the degree of crystallinity, lowering the melting temperature, lowering the glass transition temperature, increasing chain mobility, or any combination of these. A high dielectric additive can aid dissociation of the salt, increasing the number of Li+ ions available for ion transport, and reducing the bulky Li+[salt] complexes. Additives that weaken the interaction between Li+ and PEO chains/anions, thereby making it easier for Li+ ions to diffuse, may be included in the conductive phase. The additives that enhance ionic conductivity can be broadly classified in the following categories: low molecular weight conductive polymers, ceramic particles, room temp ionic liquids (RTILs), high dielectric organic plasticizers, and Lewis acids.

Other additives can be used in the polymer electrolytes described herein. For example, additives that help with overcharge protection, provide stable SEI (solid electrolyte interface) layers, and/or improve electrochemical stability can be used. Such additives are well known to people with ordinary skill in the art. Additives that make the polymers easier to process, such as plasticizers, can also be used.

In one embodiment of the invention, neither small molecules nor plasticizers are added to the block copolymer electrolyte and the block copolymer electrolyte is a dry polymer.

Further details about block copolymer electrolytes are described in U.S. Pat. No. 8,563,168, issued Oct. 22, 2013, U.S. Pat. No. 8,268,197, issued Sep. 18, 2012, and U.S. Pat. No. 8,889,301, issued Nov. 18, 2014, all of which are included by reference herein.

Fluorinated Ionic Liquid Electrolytes

Fluorinated ionic liquid electrolytes can be used in cells that have multiple electrolyte layers. Fluorinated ionic liquid electrolytes are typically immiscible with non-fluorinated electrolytes, so they can be confined to one region or layer of a cell easily. In various embodiments fluorinated ionic liquid electrolytes may include liquids, and gels, both of which can be used cells that have multiple electrolyte layers. Fluorinated ionic liquids can be especially useful as catholytes in electrochemical cells.

In some embodiments of the invention, a fluorinated ionic liquid catholyte can be described as:

in which X can be any of $CF_3SO_3$, $PF_6$, $BF_4$, FSI (bis(fluorosulfonyl)imide), FAP (tris(perfluoroalkyl)trifluorophosphate), BOB (bis(oxalate)borate), DFOB (difluoro(oxalato)borate), and/or TFSI (bis(trifluoromethane)sulfonimide); R can be any of hydrogen, alkyls, and/or branched alkyls; Rf can be any of perfluoropolyethers and/or $(CF_2)_aCF_3$, in which a is an integer greater than or equal to 2; and n is an integer greater than or equal to 1.

Such fluorinated ionic liquids can be combined with lithium salts so that they can be used as electrolytes in lithium battery cells. Examples of such salts include, but are not limited to, LiTFSI, LiFSI, $LiPF_6$, LiFAP, $LiBF_4$, $LiClO_4$, LiOTf, $LiC(Tf)_3$, LiBOB, and LiDFOB.

EXAMPLES

The following examples provide details relating to synthesis of fluorinated ionic liquids in accordance with the present invention. It should be understood the following is representative only, and that the invention is not limited by the detail set forth in these examples.

Example 1

10 mmol pyridine and 10 mmol fluorinated iodide were mixed in 50 ml acetonitrile, it was stirred at room temperature overnight. After reaction the solvent was removed by rotator evaporator. The residue was used directly for next step by mixing it with 11 mmol LiTFSI in 50 ml acetone, after it was stirred at room temperature for 4-5 hours. It was added with 500 ml DI water, the desired product phase separated out from aqueous phase, after it was separated from the aqueous phase and vacuum dried, the desired oil product was obtained.

Example 2

10 mmol pyridine and 10 mmol perfluoropolyether iodide were mixed in 50 ml acetonitrile, it was stirred at room temperature for 12 hours. After reaction the solvent was removed by rotator evaporator. The residue was used directly for next step by mixing it with 11 mmol LiTFSI in 50 ml acetone, and it was stirred at room temperature for 4-5 hours. 500 ml DI water was added and the desired product phase separated out from the aqueous phase. After it was separated from aqueous phase and vacuum dried, the desired oil product was obtained.

Example 3

10 mmol 1-methylpiperidine and 10 mmol perfluoropolyether iodide were mixed in 50 ml acetonitrile, and it was stirred at room temperature for 12 hours. After reaction the solvent was removed by rotator evaporator. The residue was used directly for next step by mixing it with 11 mmol LiTFSI in 50 ml acetone, and it was stirred at room temperature for 4-5 hours. 500 ml DI water was added and the desired product phase separated out from the aqueous phase. After it was separated from aqueous phase and vacuum dried, the desired oil product was obtained.

Example 4

10 mmol 1-methylpiperidine and 10 mmol fluorinated iodide were mixed in 50 ml acetonitrile, it was stirred at room temperature for 12 hours. After reaction the solvent was removed by rotator evaporator. The residue was used directly for next step by mixing it with 11 mmol LiTFSI in 50 ml acetone, and it was stirred at room temperature for 4-5 hours. 500 ml DI water was added and the desired product phase separated out from the aqueous phase. After it was separated from aqueous phase and vacuum dried, the desired oil product was obtained.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. An electrochemical cell, comprising: a negative electrode configured to absorb and release alkali metal ions; a positive electrode comprising a positive electrode active material, a binder, a fluorinated ionic liquid catholyte, a first salt comprising an alkali metal, and, optionally, electronically conducting carbon; a separator layer comprising a block copolymer electrolyte and a second salt comprising the alkali metal, the separator layer disposed between the negative electrode and the positive electrode and facilitates ionic communication therebetween; and wherein the fluorinated ionic liquid catholyte is immiscible with the block copolymer electrolyte; and wherein the fluorinated ionic liquid catholyte is wherein X is TFSI; R is hydrogen; Rf is $(CF2)_a CF_3$, in which a is 7; and n is 2.

2. The electrochemical cell of claim 1 wherein a first block of the block copolymer electrolyte is ionically conductive and is a polyether.

3. The electrochemical cell of claim 2 wherein a second block of the block copolymer electrolyte is polystyrene.

4. The electrochemical cell of claim 1 wherein the alkali metal comprises lithium and the first salt and the second salt are each selected independently from the group consisting of LiTFSI, LiFSI, $LiPF_6$, LiFAP, $LiBF_4$, $LiClO_4$, LiOTf, LiC$(Tf)_3$, LiBOB, and LiDFOB.

5. The electrochemical cell of claim 4 wherein the first salt and the second salt are the same.

6. The electrochemical cell of claim 1 wherein the negative electrode is a lithium-containing metal foil, and the first salt and the second salt are both lithium salts.

* * * * *